United States Patent [19]

Ogata et al.

[11] Patent Number: 5,831,025
[45] Date of Patent: Nov. 3, 1998

[54] HUMAN ACTIVATED PROTEIN C AND PROCESS FOR PREPARING SAME

[75] Inventors: Yoichi Ogata; Toshinobu Nouchi; Shinji Nakahira, all of Kumamoto, Japan

[73] Assignees: Juridical Foundation The Chemo-Sero-Therapeutic Research Institute, Kumamoto; Teijin Limited, Osaka, both of Japan

[21] Appl. No.: 637,662

[22] PCT Filed: Oct. 27, 1994

[86] PCT No.: PCT/JP94/01807

§ 371 Date: Apr. 29, 1996

§ 102(e) Date: Apr. 29, 1996

[87] PCT Pub. No.: WO95/11966

PCT Pub. Date: May 4, 1996

[30] Foreign Application Priority Data

Oct. 29, 1993 [JP] Japan ................................ 5-292499

[51] Int. Cl.$^6$ .......................... A61K 35/16; A61K 38/16; C12Q 1/56; C07K 17/14
[52] U.S. Cl. ..................... 530/380; 530/413; 530/344; 530/830; 530/856; 435/13; 435/68.1
[58] Field of Search ....................... 530/344, 380, 530/413, 830, 856; 435/13, 68.1

[56] References Cited

FOREIGN PATENT DOCUMENTS

| 0318201 | 5/1989 | European Pat. Off. . |
| 0519903 | 12/1992 | European Pat. Off. . |
| 8912685 | 12/1989 | WIPO . |
| 9112320 | 8/1991 | WIPO . |

OTHER PUBLICATIONS

Miekka et al Thrombosis and haemostasis, vol. 69, No. 6, p. 719, Jun. 30, 1993.

Orthner et al, Vox Sang, vol. 69, No. 4, pp. 309–318, 1995.

*Primary Examiner*—Ponnathapura Achutamurthy
*Assistant Examiner*—Padmashri Ponnaluri
*Attorney, Agent, or Firm*—Browdy and Neimark

[57] ABSTRACT

A human Activated Protein C preparation with a high specific activity of 3500 U/mg or more and substantially free from thrombin or other proteases which can convert Protein C into Activated Protein C is provided. A process for preparing this human Activated Protein C, which involves, contacting a solution of human Activated Protein C, after activation of Protein C with thrombin or other activating protease, with a cation exchanger to allow for adsorption of both thrombin or another activating protease and Activated Protein C to the cation exchanger followed by elution of the human Activated Protein C alone.

11 Claims, 1 Drawing Sheet

Fig.1

(Non-reductive)

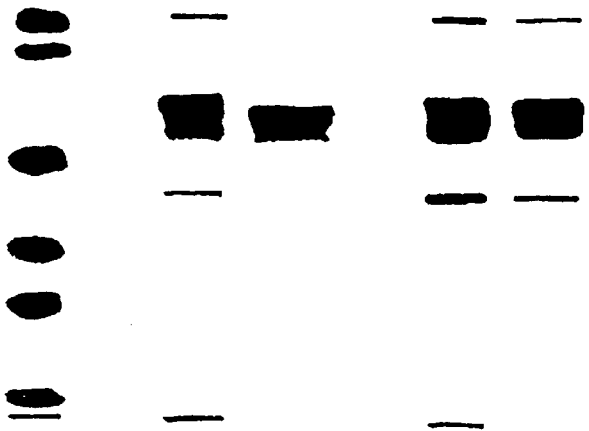

M: Molecular weight marker

A-1: Prior to treatment by the method of the present invention

A-2: After adsorption and subsequent elution (the present invention)

B-1: Prior to treatment by the conventional method

B-2: Elution fraction of the conventional method (Reductive)

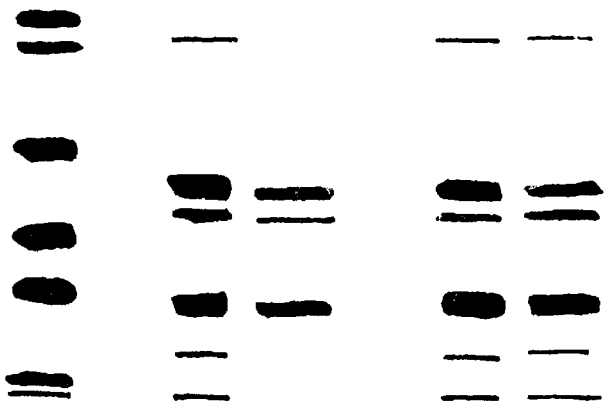

M: Molecular weight marker

A-1: Prior to treatment by the method of the present invention

A-2: After adsorption and subsequent elution (the present invention)

B-1: Prior to treatment by the conventional method

B-2: Elution fraction of the conventional method

5,831,025

HUMAN ACTIVATED PROTEIN C AND PROCESS FOR PREPARING SAME

CROSS-REFERENCE TO RELATED APPLICATIONS

This is a 371 national stage application of PCT/JP94/01807, filed Oct. 27, 1994.

TECHNICAL FIELD OF THE INVENTION

The present invention relates to a human Activated Protein C preparation having a high specific activity which is prepared by activation of human Protein C with thrombin or an equivalent protease, said Protein C being derived from plasma or prepared by using the genetic recombination technique. The present invention further relates to a method for activating human Protein C and a process for purifying human Activated Protein C a high purity.

TECHNICAL BACKGROUND

Protein C (hereinafter also abbreviated as "PC") is a kind of a vitamin K dependent protein synthesized in the liver and is an enzyme precursor having a molecular weight 62,000 consisting of two chains, i.e. L chain (molecular weight 21,000 ) and H chain (molecular weight 41,000 ). Protein C is partially degraded in vivo by a thrombin-thrombomodulin complex, thrombin bound to thrombomodulin occurring on the membrane surface of the vascular endothelial cells, and thereby a peptide comprising 12 amino acids is released from the amino terminal of H chain to form Activated Protein C (hereinafter also abbreviated as "APC"). APC is a kind of a serine protease which exhibits a strong anticoagulant activity by specific degradation and inactivation of the blood coagulation Factor V and Factor VIII (primarily activated form Va, VIIIa) and promotes the release of a plasminogen activator from the vascular wall to accelerate the fibrinolytic system. Accordingly, APC is expected to be used as a therapeutic agent.

APC itself is well known in the art and includes those obtained by in vitro activation of protein C with thrombin or thrombin-thrombomodulin complex, said protein C being derived from plasma or prepared by using the genetic recombination technique (Blood, 63, p.115–121 (1984 ); J. Clin. Invest., 64, p.761–769 (1979); J. Clin. Invest., 79, p.918–925 (1987)); or those directly expressed as APC by the genetic recombination technique (Japanese Patent First Publication (Kokai) No. 61-205487, Japanese Patent First Publication (Kokai) No. 1-2338 and Japanese Patent First Publication (Kokai) No. 1-85084), and the like.

However, for preparation of APC, especially in the case where protein C is fractionated from plasma and then activated to produce the desired protein, there are various problems need to be overcome in order to efficiently remove contaminating proteins having physico-chemical properties quite similar to APC and to highly purify APC so that APC having a desired high specific activity is obtained. For example, there still remain a number of problems to be solved with regard to efficient activation of Protein C into APC, subsequent removal of an activating agent, and purification of APC.

Known methods for activation of Protein C include, for example, activation with trypsin, RVV-X, thrombin, thrombin-thrombomodulin, activation using gel wherein RVV-X is immobilized to cepharose, activation using gel wherein thrombin-thrombomodulin complex is immobilized and the like (J. Biol. Chem., 251, 3052–3056 (1976); Biochemistry, 15, 4893–4900 (1976); Biochemistry, 16, 5824–5831 (1977); J. Clin. Invest., 64, 761–769 (1977); Biochem. Biophys. Res. Commun., 94, 340–347 (1980); J. Clin. Invest., 77, 416–425 (1986)).

However, the methods mentioned hereinabove are not satisfactory in view of production of APC on industrial scale. For activation of a large amount of Protein C, it is preferable to activate Protein C at a high concentration with a small amount of an activating agent. The above methods also do not satisfy this requirement.

As to purification of Activated Protein C after activation of Protein C, a method is known wherein APC is developed in an eluent fraction by SP-SEPHADEX chromatography and thereby thrombin added during activation of Protein C is adsorbed and removed (Biochemistry, 16, 5824–5831 (1977); J. Clin. Invest., 64, 761–769 (1979); J. Biol. Chem., 251, 3052–3056 (1976); Biochemistry, 20, 2156–2161 (1981)). However, it is hard to remove thrombin added during activation of Protein C with a cation exchanger to a clinically applicable level. Actually, the use of procedures for concentration of APC is indispensable after the procedure of the cation exchange treatment, and hence, autolysis of APC is unavoidable during concentration of APC. Accordingly, at present, an APC preparation having a high purity and high biological activity without contamination by various proteins has not yet been obtained.

DISCLOSURE OF THE INVENTION

The present invention has been made in order to solve the above-mentioned problems. The present inventors have earnestly studied, and as a result, have found that Protein C can be activated efficiently with a small amount of thrombin by using Protein C at a high concentration; that a human Activated Protein C preparation containing substantially no thrombin or equivalent protease and/or Protein C which has not been activated is obtained by contacting a solution containing Activated, Protein C after activation with a cation exchanger so that thrombin or an equivalent protease and Activated Protein C are adsorbed to the exchanger, and subsequently eluting Activated Protein C alone under a suitable salt concentration; surprisingly, the result human Activated Protein C preparation exhibits a much higher specific activity than that of human Activated Protein C obtained by the conventional method. An object of the present invention is to provide a human Activated Protein C preparation with a high specific activity substantially free from thrombin or an equivalent protease and/or Protein C which has not been activated and a process for preparing the same.

BRIEF DESCRIPTION OF THE DRAWING

FIG. 1 shows the results of SDS-PAGE for the preparation of the present invention and the conventional preparation.

BEST MODE FOR CARRYING OUT THE INVENTION

The human Activated Protein C preparation of the present invention shows specific activity of 3500 U/mg or more, the unit of specific activity being defined as an amount which prolongs twice an activated thromboplastin time (APTT) of normal human plasma, and is substantially free from thrombin or an equivalent protease and/or Protein C which has not been activated. In accordance with the process for preparing the preparation of the present invention, after activation of human Protein C with thrombin or an equivalent protease, a solution containing human Activated Protein C is contacted with a cation exchanger under condition of pH 5.0 to 6.0, an NaCl concentration of 80 mM or less, to allow for adsorption of thrombin and Activated Protein C to the exchanger, and then human Activated Protein C alone is eluted with a salt concentration of 0.1 to 0.35M to solely recover a highly purified human Activated Protein C.

For activation of Protein C in the above solution containing Protein C with thrombin or an equivalent protease, thrombin is added to a solution containing Protein C at a concentration of 0.5 to 8.0 mg/ml at a thrombin/Protein C ratio of 1 to 20 U/mg and activation is conducted under pH 6.0 to 8.0 to efficiently activate a large amount of Protein C. Subsequent to this step, procedures for removal of the activating agent and purification of APC are carried out wherein a solution containing APC after activation is contacted with a cation exchanger under condition of pH 5.0 to 6.0, NaCl concentration of 80 mM or less, to allow for adsorption of both thrombin and APC to the exchanger and then Activated Protein C alone is eluted therefrom with a salt concentration of 0.1 to 0.35M.

In accordance with the method for activating human Protein C of the present invention, it is possible to efficiently activate Protein C at a high concentration with a small amount of thrombin. This is advantageous in that degradation of Protein C during activation is decreased and the subsequent removal of thrombin becomes easier. Subsequent procedure for purification of APC provides a thrombin concentration in the eluent of 0.001 U/ml or less, and hence, APC can be recovered quantitatively. Furthermore, a concentrated APC can be obtained since APC is eluted after adsorption thereof. In addition, the APC preparation recovered by the method of the present invention has a much higher specific activity than the preparations obtained by the conventional methods.

"Specific activity" of the human Activated Protein C preparation as used herein means a ratio of APC activity to a whole amount of protein (mg). One Unit of APC activity is defined as an amount which prolongs twice an activated thromboplastin time (APTT) of normal human plasma. Accordingly, actual measurement of APC activity is conducted as follows: the APTT (second) is measured for normal human plasma to which a diluted sample is added and the dilution at which the measured APTT value is twice that of control (buffer) is determined to be the activity of APC of sample.

The main component of the preparation of the present invention, APC, and the starting material of the process for preparation of the present invention, Protein C, may be derived from any source, but preferably from human plasma.

The activation step in the above-mentioned procedures of the present invention is conducted as follows: thrombin is added to a solution containing Protein C at a concentration of 0.5 to 8.0 mg/ml at a ratio of thrombin/Protein C of 1 to 20 U/mg, and the reaction is carried out under condition of pH 6.0 to 8.0, a salt concentration of 0.1 to 0.15M, for example, at 37° C. for 5 to 6 hours.

The resultant reaction solution of the above activation procedure, after adjustment of pH or salt concentration as desired, is then subjected to treatment with a cation exchanger to purify APC. This treatment with a cation exchanger removes thrombin and further contaminating proteins such as Protein C which have not been activated. A cation exchanger as used herein may be any exchanger as far as it is an insoluble carrier having a cation-exchange group (e.g. sulfo group, carboxyl group), and includes a cation exchanger which is conventionally used in the art, for example, a cation exchange resin such as S-SEPHAROSE (trade name for a methyl sulfonate bound cation exchanger based on agarose), S-SEPHAROSE (trade name for sulfopropyl bound cation exchanger based on dextran), both manufactured by Pharmacia, SP-TOYOPEARL (trade name for sulfopropyl bound cation exchanger based on a hydrophilic vinyl polymer), TSK GEL SP-5PW (trade name), both manufactured by Toyo Soda K.K. Among these, SP-SEPHADEX and SP-TOYOPEARL are preferable. This step may be carried out either by a column process or a batch process. In view of the removal efficiency of contaminating proteins, a column process is preferable.

The purification procedure of APC in accordance with the present invention is characteristic in that the reaction solution of activation is contacted with a cation exchanger to allow for adsorption of both thrombin and APC to the exchanger and then Activated Protein C alone is eluted therefrom under condition of a salt concentration 0.1 to 0.35M. The APC preparation prepared by such purification procedure is substantially free from thrombin or an equivalent protease and/or Protein C which has not been activated and has an extremely high specific activity of 3500 U/mg or more.

Furthermore, the present inventors have also studied in order to eliminate defects of the conventional method in a series of steps for preparing APC having a high specific activity starting from a fraction of Protein C, and as a result, have found several useful improvements to further enhance the effects of the present invention.

For purification of Protein C, there have been known a method wherein Protein C, after being purified by adsorption and precipitation with barium citrate, fractionation with ammonium sulfate, and DEAE-SEPHADEX (trade name for diethylaminoethyl bound anion exchanger based on dextran column chromatography, is further subjected to purification procedures such as preparative polyacrylamide gel electrophoresis, dextran sulfate agarose chromatography, etc. or a method for purification of Protein C by using a gel to which an antibody against Protein C is immobilized, and the like (J. Biol. Chem., 251, 355–363 (1976); J. Clin. Invest., 64, 761–769 (1979); Blood, 54, 1272–(1979); FEBS LETTERS, 191, 75–81 (1985); J. Bio. Chem., 261, 11097–11105 (1986)). The above-mentioned methods, however, are suitable for the laboratory, but are not suited for industrial large scale purification when consideration is given to yield, working efficiency, etc. It is further noted that in case of purification with a gel to which an antibody against Protein C is immobilized, a strong chaotropic ion or acidic pH or a strong chelating agent such as EDTA for elution is utilized, but a trace amount of the antibody against Protein C is disadvantageously released from the gel and contained in the eluent.

The present inventors have found that release of the antibody against Protein C from the gel is diminished by eluting Protein C with a citrate buffer solution in place of a strong chelating agent, EDTA. The obtained solution containing Protein C is then contacted with an anion exchanger under condition of pH 7.0 to 9.0 to allow for adsorption of Protein C to the exchanger, thereby removing a trace amount of the antibody against Protein C, followed by elution of Protein C under condition of a salt concentration of 0.3 to 1.0M. This procedure can remove almost all the antibody against Protein C.

Based on the above findings, an improved process for preparing Activated Protein C on an industrial scale is provided in accordance with the present invention, said process comprises the following steps:

(1) a solution containing human Protein C is contacted with an anion exchanger to allow for adsorption of Protein C to the exchanger, and thereafter Protein C is eluted to prepare a fraction of human Protein C having a Gla domain;

(2) the solution containing human Protein C is contacted with an adsorbent, i.e. an insoluble carrier to which an antibody specifically recognizing Protein C bound with calcium ion is attached, in the presence of calcium to allow for adsorption of Protein C to the adsorbent, and then Protein C is eluted therefrom using a citrate buffer solution;

(3) the solution containing Protein C is contacted with an anion exchanger to allow for adsorption of Protein C to the exchanger, and thereafter Protein C is eluted therefrom to remove the antibody against Protein C from the above solution containing Protein C;

(4) human Protein C is activated with thrombin or an equivalent protease wherein thrombin is added to the solution containing Protein C at a ratio of thrombin/Protein C 1 to 20 U/mg under condition of pH 6.0 to 8.0; and then (5) the solution containing human Activated Protein C after activation is contacted with a cation exchanger under condition of pH 5.0 to 6.0, a salt concentration of 80 mM or less, to allow for adsorption of both thrombin and Activated Protein C to the exchanger, and then human Activated Protein C alone is eluted therefrom with a salt concentration of 0.1 to 0.35M and recovered.

In the case of using purified Activated Protein C for therapy, especially when purified Activated Protein C is derived from human plasma, there is a risk of infection with viruses that may be present in source material (e.g. hepatitis virus, HIV, etc.), and hence, removal and inactivation of viruses is necessary. Protection from viral infection in case of blood preparations has been carried out by removal of viruses by screening of source material, membrane filtration, adsorption, column chromatography, precipitation, fractionation, or inactivation by a solvent detergent method, β-propiolactone, heating, electromagnetic radiation, etc., or in combination thereof. However, it is difficult to remove and inactivate viruses without causing denaturation of a protein, decrease in physiological activity, decrease in yield, etc. The present inventors have found that removal and inactivation of viruses can effectively be conducted for Activated Protein C preparation by removal of viruses with a membrane filtration using a virus-removing membrane in combination with freeze-dry heating using as a stabilizing agent albumin at 0.5 to 10% (W/V). With such procedure, viruses can effectively be removed and inactivated without causing denaturation of Activated Protein C, decrease in physiological activity and yield.

The present inventors have studied for developing an efficient process for purification and activation of Protein C and further a means for protection from viral infection for therapeutic use, and as a result, have found that the use of a citrate buffer solution for elution in purification of Protein C by affinity chromatography using an antibody against Protein C; activation of Protein C at a high concentration; and purification of Activated Protein C by adsorption to a cation exchanger are effective. Based on these purification procedures, and in combination with removal of viruses with a virus-removing membrane and viral inactivation by freeze-dry heating, the present inventors have established the technique to efficiently produce a large amount of Activated Protein C of a high purity for therapeutical application in high yield.

The APC preparation of the present invention, in addition to its decreased level of contaminating proteins, is characteristic in that it shows a higher specific activity (APC activity/whole amount of protein (mg)) than those of APCs prepared by the conventional methods, for example, by the method disclosed in Biochemistry, 16, 5824–5831 (1977). In fact, the APC preparation of the present invention shows a specific activity 1.5 times to twice higher than that of the conventional preparations. The main reason why such increase in specific activity was observed remains still unclear, but it is estimated that removal of contaminating proteins (degradated products of APC, Protein C not being subjected to activation, coagulated proteins, etc.), which the conventional methods could not attain, may be one of main factors.

The present invention is illustrated in more detail by means of the following examples, but should not be construed to be limited thereto.

EXAMPLE 1

1.1 Preparation of Activated Protein C preparation having a high specific activity A solution of Protein C preparation derived from plasma (8.7 mg/ml of Protein C, pH 7.5, 34.3 ms/cm of conductivity) was dialyzed against 20 mM citrate/0.1M sodium chloride buffer (pH 6.0) and then diluted to a concentration of 4 mg/ml of Protein C. To this solution was added human thrombin at a final concentration of 60 U/ml and the mixture was heated at 37° C. for 5 hours to activate Protein C.

After activation, the solution after activation was diluted twice with 20 mM citrate buffer (pH 6.0) and applied to a column of a cation exchanger (SP-TOYOPEARL) for removal of thrombin. The exchanger was washed well with 20 mM citrate buffer (pH 6.0) containing 60 mM sodium chloride and then Activated Protein C was eluted with 20 mM citrate buffer (pH 6.0) containing 0.3M sodium chloride. Under this condition, Activated Protein C alone was eluted without elution of thrombin. A concentration of remaining thrombin was 0.001 U/ml or less. The obtained APC preparation showed a specific activity of 4750.9 U/mg.

1.2 Study for condition of APC adsorption and elution in a cation chromatography after activation (1) Adsorption condition Using 20 mM citrate buffer, an adsorption condition of APC was examined within a range of pH 6.0 to 7.0 and a salt concentration of 0.0 to 0.15M which can be applicable in view of stability of APC. Adsorption of APC hardly occurred at a condition of pH 7.0 and a salt concentration of 0.1M. At a condition of pH 6.5 and a salt concentration of 0.1M, most of APC was eluted although it was partly adsorbed. At a condition of pH 6.0 and a salt concentration of 0.1M, most of APC was adsorbed onto the chromatographic carrier.

Based on these results, a degree of APC adsorption was studied using a fixed pH 6.0 and various salt concentrations. At a salt concentration of 0.15M, not only APC but also a part of thrombin used for activation were eluted, whereas at a salt concentration of 0.1M, most of APC was adsorbed but adsorption was not sufficient and a part of APC was eluted as mentioned above. Thus, a salt concentration was adjusted at 80 mM and thereby a suitable adsorption of APC to the chromatographic carrier was observed.

(2) Elution condition

After the chromatographic carrier was equilibrated with 20 mM citrate buffer (pH 6.0) containing 60 mM NaCl, a gradient elution was conducted at a concentration of 60 mM to 0.5M NaCl. Elution of APC started gradually at a concentration of around 0.1M NaCl, and at 0.35M or more, thrombin was also partially eluted. Accordingly, a preferable elution condition is a concentration of less than 0.35M NaCl.

Reference Example 1
Preparation of Activated Protein C preparation by the conventional method The above solution of Protein C preparation (8.7 mg/ml of Protein C, pH 7.5, 34.3 ms/cm of conductivity) was dialyzed against 50 mM Tris-HCl/0.1M sodium chloride buffer (pH 8.0) and then diluted to a concentration of 0.7 mg/ml of Protein C. To this solution was added thrombin at a final concentration of 10 U/ml and the mixture was heated at 37° C. for 5 hours to activate Protein C. After activation, the reaction solution was applied to a column of a cation exchanger (SP-TOYOPEARL), which was previously washed and equilibrated with 50 mM Tris-HCl/0.15M sodium chloride buffer (pH 8.0), and thereby thrombin was adsorbed and Activated Protein C was recovered in an elution fraction. A specific activity of Activated Protein C in this solution was 3259.6 U/mg.

EXAMPLE 2
Comparison of the preparation of the present invention with the conventional preparations The preparations of Example 1 and Reference Example 1 were compared for their specific activity and purity using electrophoresis, etc.

2.1 Measurement of Activated Protein C activity:

The activity of APC was measured herein in accordance with the following procedures.

One unit of APC activity is defined as an amount of APC which prolongs twice an activated thromboplastin time (APTT; second) to double that of normal human plasma. Accordingly, the activity of APC is measured wherein APTT (second) is measured for a normal human plasma to which a diluted sample is added and the dilution at which the measured APTT value is twice as that of control (buffer) is determined and regarded as the activity of APC for samples.

(Procedures)

A sample was diluted with a veronal buffer containing 1% HSA to, for example, 400 times, 500 times, 800 times or 1000 times dilution. To each 100 μl of either control (buffer) or samples of each dilution were added 100 μl of normal human plasma (e.g. Citrol I: Baxter Diagnostics Inc.) and 100 μl of APTT reagent (e.g. Actin: Baxter Diagnostics Inc.) at 37° C. successively with an interval of 15 seconds, the mixture is stirred, and after 2 minutes, 0.025M CaCl$_2$ 100 μl is added and a coagulation time is measured.

(Calculation of activity)

A linear regression formula and a correlation coefficient of $10^3/X$ and Y are obtained from values of APTT (Y) at each dilution (X) of control and samples as follows:

$$Y = A(10^3/X) + B$$

A value of $X_1$ obtained from the following formula:

$$X_1 = 10^3\{(Y_1 - B)/A\}$$

wherein $Y_1$ is a value twice that of APTT (second) of control, is regarded as the activity of APC (U/ml) for samples.

(Measurement of protein)

A concentration of Activated Protein C was measured based on measurement of absorbance $A_{280}$, i.e. based on the estimation that $A_{280}$ of APC at a concentration of 1% (W/V) (10 mg/ml) is 14.5 as estimated from an amino acid composition of APC (J. Clin. Invest., 64, 761–769 (1979)). Accordingly, a concentration of Activated Protein C is calculated by the following formula:

Concentration of Activated Protein C (mg/ml)=$A_{280}$ as measured/1.45

Based on the activity and the concentration of APC measured above, a specific activity of APC (U/mg) as used herein was calculated.

2.2 Effect of the activation conditions on specific activity of APC

Using samples just after activation, effect of difference in activation condition on a specific activity was studied. Measurement of APC activity after activation was conducted wherein each 1 U and 10 U of anti-thrombin and heparin was added to 1 ml of a sample before measurement and the mixture was heated at 37° C. for 30 minutes to inactivate thrombin. The results are shown in Table 1. No effect on specific activity was observed for the activation condition of the present invention (pH 6.0, NaCl concentration 0.1M) as compared to the activation condition of the conventional method (pH 8.0, NaCl concentration 0.15M).

TABLE 1

|  | Conventional method | Present invention |
| --- | --- | --- |
| Concentration of protein (mg/ml) | 0.72 | 1.38 |
| Activity (U/ml) | 2069.9 | 4133.4 |
| Specific activity (U/mg) | 2885.9 | 3089.3 |

2.3 Comparison of specific activity before and after treatment with cation chromatography Using various samples, a specific activity of APC before and after treatment with a cation chromatography in accordance with the present invention was compared. The results are summarized in Table 2. Increase in specific activity was barely observed in the conventional preparation. On the contrary, the preparations of the present invention showed specific activity of APC (U/mg) of more than 4500, specific activity of APC being increased by about 1.5 times after the chromatography treatment. The main reason why such increase in specific activity was observed remains still unclear, but it is estimated that removal of contaminating proteins (degraded products of APC, Protein C which has not been activated, coagulated proteins, etc.), which the conventional methods could not remove, may be one of main factors.

TABLE 2

| Sample | Specific activity (U/mg) | | Rate of increase (times) |
| --- | --- | --- | --- |
|  | Before Chromatography | After | |
| Invention 1 | 3089.3 | 4750.9 | 1.54 |
| Invention 2 | 3108.3 | 5750.5 | 1.85 |
| Invention 3 | 3869.5 | 5107.8 | 1.32 |
| Conventional preparation | 2885.9 | 3259.6 | 1.13 |

2.4 Comparison with electrophoresis before and after treatment with cation chromatography APC has been eluted at pH 8.0 in the procedure of a cation chromatography in the conventional method whereas, in the method of the present invention, APC is first adsorbed at pH 6.0 and then eluted. FIG. 1 shows results of SDS-PAGE in the conventional method and the method of the present invention.

In accordance with the method of the present invention wherein APC is adsorbed at pH 6.0 and Protein C which has not been activated is eluted, fraction bands of those regions having higher or lower molecular weight than that of APC are removed. In addition, in comparison with the fraction eluted at pH 8.0, the fraction obtained by adsorption at pH 6.0 and a subsequent elution showed a sharper band of the corresponding APC, and hence, Protein C which has not been activated is possibly removed. On the other hand, although the eluted fraction obtained by the conventional method showed some quantitative decrease in fraction bands having higher or lower molecular weight than that of APC, these bands were not perfectly removed.

2.5 Content of Protein C not being subjected to activation in APC preparation

Decreased content of Protein C which has not been activated was considered to be one of the factors which led to an increase in specific activity of the APC preparation of the present invention having a high specific activity. Thus, a content of Protein C which has not been activated was measured for both the APC preparations of the present invention and the conventional preparations. Measurement was made by employing ELISA system using a monoclonal antibody specific for Protein C in accordance with the usual protocol. The results are shown in Table 3.

TABLE 3

| Sample | Specific activity of APC (U/mg) | Content of Protein C which has not been activated |
|---|---|---|
| Present preparation 1 | 5750.5 | 0.47 |
| Present preparation 2 | 5107.8 | 1.22 |
| Present preparation 3 | 4457.1 | 0.36 |
| Conventional preparation 1 | 2661.7 | 5.41 |
| Conventional preparation 2 | 3286.2 | 5.83 |
| Conventional preparation 3 | 2470.4 | 3.93 |

The conventional preparations having a low specific activity had a content of 4 to 6% Protein C which has not been activated whereas the preparations of the present invention having a high specific activity had a content of as little as 0.4 to 1.2%. Although the conventional preparations do have a higher content of Protein C which has not been activated as compared to that of the preparations of the present invention, the content is very small, and hence, is not liable to exert a direct effect on specific activity of the preparations. In order to confirm this, to the preparation 3 of the present invention having the smallest content of Protein C not being subjected to activation was added Protein C at a final concentration of 5% and the APC activity (APTT) was measured. As a result, no change was observed in APTT values as compared to the case without addition of Protein C (cf. Table 4). Accordingly, decrease in content of Protein C which has not been activated is not thought to be a main factor for increase in specific activity of APC as observed in the preparations of the present invention.

TABLE 4

| | Specific activity of APC (U/mg) | |
|---|---|---|
| Sample | Without addition of Protein C | With addition of 5% Protein C |
| Present preparation 3 | 5077.9 | 5173.7 |
| Conventional preparation 3 | 2726.0 | 2725.7 |

EXAMPLE 3

Preparation of Activated Protein C preparation

Industrial scale quanity of fresh frozen human plasma (100 L) was melted without heating and precipitates formed were separated by centrifugation. The obtained supernatant was added to an anion exchanger (DEAE-SEPHADEX A-50). The exchanger was well washed with 20 mM citrate buffer (pH 7.0) containing 0.1M sodium chloride and elution with 20 mM citrate buffer (pH 7.0) containing 0.5M sodium chloride was carried out to elute a fraction of human Protein C having a Gla domain.

To this solution was added 30 mM calcium chloride and then the mixture was applied to a column of affinity chromatography using an anti-Protein C antibody. The column was well washed with 50 mM Tris-HCl buffer (pH 8.0) containing 0.15M sodium chloride and 2 mM calcium chloride and thereafter Protein C was eluted with 20 mM citrate buffer (pH 6.0) containing 0.15M sodium chloride.

This solution was adjusted to pH 8.0 with 0.1M sodium hydroxide and then added to a column of an anion exchanger (Q-SEPHAROSE Fast Flow a quaternary ammonium bound anion exchanger). The exchanger was well washed with 50 mM Tris-HCl buffer (pH 8.0) containing 0.15M sodium chloride and elution was conducted with 0.3M glycine buffer (pH 7.0) containing 0.4M sodium chloride. Protein C obtained in this step was confirmed to be a single band in SDS-PAGE.

For activation, the solution of purified Protein C obtained by the above procedure was diluted with 20 mM citrate buffer (pH 6.0) to a concentration of 4 mg/ml of Protein C. To this solution was added thrombin at a final concentration of 60 U/ml and the mixture was heated at 37° C. for 5 hours to activate Protein C.

After activation, for removal of thrombin, the solution after activation was twice diluted with 20 mM citrate buffer (pH 6.0) and applied to a column of a cation exchanger (SP-TOYOPEARL). The exchanger was well washed with 20 mM citrate buffer (pH 6.0) containing 60 mM sodium chloride and then Activated Protein C was eluted with 20 mM citrate buffer (pH 6.0) containing 0.35M sodium chloride. Under this condition, Activated Protein C alone was eluted without elution of thrombin and thereby thrombin is removed. The obtained solution of Activated Protein C was subjected to filtration with a virus-removing membrane (Planova 35N manufactured by Asahi Chemical Industries, K.K.). The resultant solution had 5392.7 U/mg of specific activity of Activated Protein C and 0.001 U/ml or less of a concentration of remaining thrombin.

The filtrate was adjusted to 0.7% (W/V) sodium chloride, 0.5% (W/V) glycine, 0.6% (W/V) sodium citrate, 2.5% (W/V) human albumin and 600 U/ml of the activity of APC at a final concentration. The solution of Activated Protein C thus prepared was subjected to sterile filtration, freeze-drying, and then dry-heated at 65° C. for 96 hours for inactivation of viruses to ultimately give Activated Protein C suitable for therapeutic application.

What is claimed is:

1. A human Activated Protein C preparation with a specific activity of 3500 U/mg or more, the unit of specific activity being defined as an amount of Activated Protein C which prolongs twice an activated thromboplastin time (APTT) of normal human plasma, and is substantially free from a protease, which converts Protein C into Activated Protein C, and/or starting Protein C zymogen used for activation.

2. The human Activated Protein C preparation of claim 1 wherein the specific activity is 4000 U/mg or more.

3. The human Activated Protein C preparation of claim 1, wherein said preparation is prepared by activation with protease which converts human Protein C into Activated Protein C.

4. A process for purification of human Activated Protein C which comprises, after activation of human Protein C with a protease which converts Protein C into Activated Protein C, a protease which can convert Protein C into Activated Protein C, contacting a solution containing human Activated Protein C with a cation exchanger under conditions of pH 5.0 to 6.0 and a salt concentration of 80 mM or less, to allow for adsorption of a protease and Activated Protein C to the exchanger, and eluting human Activated Protein C alone with a salt concentration of 0.1 to 0.35M, wherein said eluted human Activated Protein C is substantially free from a protease, which converts Protein C into Activated Protein C, and/or starting Protein C zymogen used for activation.

5. A process for preparing the human Activated Protein C preparation of claim 1, said process comprising the following steps:

(1) contacting a solution containing human Protein C with an anion exchanger to allow for adsorption of Protein C to the exchanger, and then eluting Protein C to prepare a fraction of human Protein C having the calcium-binding γ-carboxyglutamic acid (Gla) domain;

(2) contacting the solution containing human Protein C with an adsorbent ion is attached, in the presence of calcium to allow for adsorption of Protein C to the absorbent, and then eluting Protein C therefrom using a citrate buffer solution;

(3) contacting the solution containing Protein C with an anion exchanger to allow for adsorption of Protein C to the exchanger, and then eluting Protein C therefrom to remove the antibody against Protein C from the above solution containing Protein C;

(4) activating human Protein C with a protease which converts Protein C into Activated Protein C, wherein a protease is added to the solution containing Protein C at a ratio of a protease/Protein C of 1 to 20 U/mg under pH conditions 6.0 to 8.0; and (5) contacting the solution containing human Activated Protein C after activation with a cation exchanger under conditions of pH 5.0 to 6.0 and a salt concentration of 80 mM or less, to allow for adsorption of both thrombin and Activated Protein C to the exchanger, and then eluting human Activated Protein C alone therefrom with a salt concentration of 0.1 to 0.35M for recovery.

6. The process according to claim 5, wherein, in step (2), the adsorbent is an insoluble carrier to which an antibody that specifically recognizes Protein C bound with calcium ion is attached.

7. A large scale human Activated Protein C preparation prepared by the process of claim 4, which has a specific activity of 3500 U/mg or more, wherein the unit of specific activity being defined as an amount of Activated Protein C which prolongs twice an activated thromboplastin (APTT) of normal human plasma.

8. A human Activated Protein C preparation according to claim 1, wherein the protease is thrombin.

9. A human Activated Protein C preparation according to claim 3, wherein the protease is thrombin.

10. A process for purification of human Activated Protein C according to claim 4, wherein the protease is thrombin.

11. A process for preparing human Activated Protein C according to claim 5, wherein the protease is thrombin.

* * * * *